United States Patent
Havemann et al.

(10) Patent No.: US 10,094,735 B2
(45) Date of Patent: Oct. 9, 2018

(54) PLASTIC TUBE SEALING AND TEST SYSTEM

(71) Applicant: AnC Precision Machining Inc., Palmdale, CA (US)

(72) Inventors: Gregory Havemann, Gardnerville, NV (US); John M. Sweeney, Palmdale, CA (US)

(73) Assignee: AnC Precision Machining Inc., Palmdale, CA (US)

( * ) Notice: Subject to any disclaimer, the term of this patent is extended or adjusted under 35 U.S.C. 154(b) by 0 days.

(21) Appl. No.: 14/832,759

(22) Filed: Aug. 21, 2015

(65) Prior Publication Data

US 2015/0362399 A1    Dec. 17, 2015

Related U.S. Application Data

(60) Division of application No. 13/573,228, filed on Aug. 31, 2012, now Pat. No. 9,146,184, which is a
(Continued)

(51) Int. Cl.
*G01N 3/12* (2006.01)
*G01M 3/28* (2006.01)
(Continued)

(52) U.S. Cl.
CPC ......... *G01M 3/2846* (2013.01); *B29C 65/103* (2013.01); *B29C 65/7841* (2013.01);
(Continued)

(58) Field of Classification Search
CPC .... G01M 3/2807; G01M 3/2846; G01N 3/12; B29C 65/8246
See application file for complete search history.

(56) References Cited

U.S. PATENT DOCUMENTS

| 2,935,831 A | 5/1960 | Saumsiegle |
| 3,243,085 A * | 3/1966 | Wilson ................ B67D 1/0412 137/209 |

(Continued)

FOREIGN PATENT DOCUMENTS

| JP | 2009-190785 A | 8/2009 |
| WO | 02/44026 A1 | 6/2002 |

OTHER PUBLICATIONS

Jacomex SAS, "Tube Tester," retrieved from http://www.jacomex.fr/en/equipments/cosmetic-equipments/cosmetic/equipment/tube-tester/ on Sep. 17, 2015, 5 pages.
(Continued)

*Primary Examiner* — Lisa Caputo
*Assistant Examiner* — Alex Devito
(74) *Attorney, Agent, or Firm* — Seed IP Law Group LLP

(57) ABSTRACT

A tube sealing positioning apparatus has a tube holder slidable on a vertical guide from a lower to an upper portion of a sealing chamber for positioning adjacent a heating apparatus and a clamping apparatus. The heating apparatus may have a nozzle to direct heated air on an open end of a plastic tube. The clamping apparatus may have two clamping devices slidably disposed to clamp the heated open end of the plastic tube to fuse the tube wall adjacent the open end. A control processor may be connected to control movement and dwell time of the tube holder, and to control heat application and clamp spacing and time. A sealed tube may be attached to a top cover to be positioned in a test container. A sealing disk may close the top cover and may direct fluid pressure into the tube and apply a vacuum to the test container.

24 Claims, 9 Drawing Sheets

Related U.S. Application Data continuation-in-part of application No. 12/291,298, filed on Nov. 6, 2008, now abandoned.

(51) Int. Cl.

| | | |
|---|---|---|
| *G01N 3/06* | (2006.01) | |
| *B29C 65/78* | (2006.01) | |
| *B29C 65/82* | (2006.01) | |
| *B29C 65/00* | (2006.01) | |
| *G01M 3/32* | (2006.01) | |
| *B29C 65/10* | (2006.01) | |
| *G01N 3/00* | (2006.01) | |
| *G01N 3/08* | (2006.01) | |
| *B29L 23/20* | (2006.01) | |

(52) U.S. Cl.
CPC ...... *B29C 65/8246* (2013.01); *B29C 66/1122* (2013.01); *B29C 66/43121* (2013.01); *B29C 66/8163* (2013.01); *B29C 66/8167* (2013.01); *B29C 66/8181* (2013.01); *B29C 66/81427* (2013.01); *B29C 66/8223* (2013.01); *B29C 66/8224* (2013.01); *B29C 66/8225* (2013.01); *B29C 66/8242* (2013.01); *B29C 66/83221* (2013.01); *B29C 66/841* (2013.01); *B29C 66/9121* (2013.01); *B29C 66/9141* (2013.01); *B29C 66/9241* (2013.01); *B29C 66/92211* (2013.01); *B29C 66/92611* (2013.01); *B29C 66/92655* (2013.01); *B29C 66/944* (2013.01); *B29C 66/9492* (2013.01); *B29C 66/96* (2013.01); *B29C 66/9674* (2013.01); *G01M 3/3209* (2013.01); *G01M 3/329* (2013.01); *G01N 3/00* (2013.01); *G01N 3/06* (2013.01); *B29C 66/43123* (2013.01); *B29C 66/961* (2013.01); *B29L 2023/20* (2013.01); *G01N 3/08* (2013.01)

(56) References Cited

U.S. PATENT DOCUMENTS

| | | | | |
|---|---|---|---|---|
| 3,430,485 A | * | 3/1969 | Henry, Jr. | G01M 3/2846 346/33 R |
| 3,465,572 A | * | 9/1969 | Covert | G01M 3/24 73/41 |
| 3,554,006 A | * | 1/1971 | Windle | G01N 3/12 73/49.5 |
| 3,620,774 A | | 11/1971 | Ford et al. | |
| 3,751,973 A | * | 8/1973 | Strauss | G01M 3/02 73/45 |
| 3,823,306 A | | 7/1974 | Davis | |
| 3,895,514 A | * | 7/1975 | Northup | G01N 3/12 73/49.4 |
| 4,012,944 A | * | 3/1977 | Covington | G01M 3/2807 73/40.5 R |
| 4,237,723 A | * | 12/1980 | Kent | G01N 3/12 73/49.6 |
| 4,285,230 A | * | 8/1981 | Hartness | G01N 3/12 73/37 |
| 4,459,843 A | * | 7/1984 | Durham | G01M 3/3236 73/37 |
| 4,576,661 A | | 3/1986 | Persson | |
| 4,727,707 A | | 3/1988 | Hadden | |
| 4,763,511 A | | 8/1988 | Mathison et al. | |
| 5,172,583 A | | 12/1992 | Tallon | |
| 5,238,172 A | | 8/1993 | Le Davay | |
| 5,365,774 A | | 11/1994 | Horlacher | |
| 5,375,888 A | | 12/1994 | Ikeda | |
| 5,463,851 A | | 11/1995 | Nagai | |
| 5,528,925 A | | 6/1996 | Sherepa et al. | |
| 5,649,406 A | | 7/1997 | Sonntag et al. | |
| 5,816,019 A | | 10/1998 | Saget et al. | |
| 6,598,367 B2 | | 7/2003 | Nakagawa et al. | |
| 7,464,518 B2 | | 12/2008 | Ansinn | |
| 8,650,934 B1 | | 2/2014 | Levy | |
| 2003/0209823 A1 | | 11/2003 | Waring et al. | |
| 2005/0028926 A1 | | 2/2005 | Tsaur | |
| 2006/0048486 A1 | | 3/2006 | Laing et al. | |
| 2006/0179922 A1 | * | 8/2006 | Sacca | G01M 3/3218 73/49.2 |
| 2007/0187877 A1 | | 8/2007 | Hansen | |
| 2009/0000355 A1 | | 1/2009 | Pernel | |
| 2010/0089128 A1 | | 4/2010 | Vasshus et al. | |
| 2010/0107569 A1 | | 5/2010 | Havemann et al. | |
| 2014/0224337 A1 | | 8/2014 | Zikeli et al. | |

OTHER PUBLICATIONS

Norden Machinery AB, "Norden In-Line Leak Testing," retrieved from http://www.nordenmachinery.com/en/home/innovation/Leak_Testing on Sep. 17, 2015, 2 pages.

* cited by examiner

PLASTIC TUBE SEALING AND TEST SYSTEM

BACKGROUND OF THE INVENTION

This invention relates to systems used to seal one end of a plastic tube that may be used to hold fluid products such as tooth paste, creams, lotions, grease and the like. The plastic tube may have a mouth end with a threaded cap or other closure element. The new system may have a tube sealing apparatus with various electronic sensing and control elements and may be combined with a tube seal and wall strength test apparatus.

Systems that may be used to fill flexible plastic tubes through an open end with a fluid product and then seal the open end may be currently known. These systems for high volume production may have a tube conveyor on which the tube open end may be oriented upwardly to receive product from a dispensing device. The tube may then be conveyed to a heating device such as a hot air blower to heat the plastic to a selected temperature approximately the melting point of the plastic and then be conveyed to a jaw clamping device to press or crimp the open end plastic wall together to heat seal the open end.

While this may be considered a relatively simple process, various parameters associated with plastic tubes, for example, thickness of walls or other dimensions, and plastic composition that may affect the melt flow index, may affect the quality of the tube heat seal. Currently known methods for producing product filled plastic tubes may not incorporate testing methods and apparatus to test plastic tubes to ensure the tubes will be properly sealed in production to avoid failure of the seal or the wall of a tube when delivered to the consumer.

SUMMARY OF THE INVENTION

The present invention is directed to apparatus for plastic tube sealing and testing. A housing may have in a sealing chamber a tube sealing positioning apparatus with a tube holder slidable on a vertical guide from a lower portion to an upper portion to be positioned adjacent a heating apparatus and a clamping apparatus. The tube holder may be moved and positioned by a linear positioning device. The heating apparatus may have a nozzle to direct heated air on an open end of a plastic tube. The clamping apparatus may have two clamping devices slidably disposed to clamp the heated open end of the plastic tube to fuse the tube wall adjacent the open end. A spacing distance sensor and a tube position distance sensor may be attached to the clamping devices for sensing the position of the tube and the spacing of the clamp jaws of the clamping devise. A control processor may be connected to the linear positioning device to control movement and dwell time of the tube holder. The heating apparatus and clamp positioning device may be connected to the control processor to control heat application and clamp jaw spacing and clamp time. A sealed tube may be attached to a top cover of a test container to be positioned in the test container. A sealing disk may be positioned on the top cover to close an aperture in the cover. The sealing disk may have a port to direct a fluid pressure into a mouth of the tube and a port to apply a vacuum to the test container. The control processor may control the amount of pressure or vacuum applied on a time basis for conducting a test.

These and other features, aspects and advantages of the present invention will become better understood with reference to the following drawings, description and claims.

DETAILED DESCRIPTION

Figure 1:
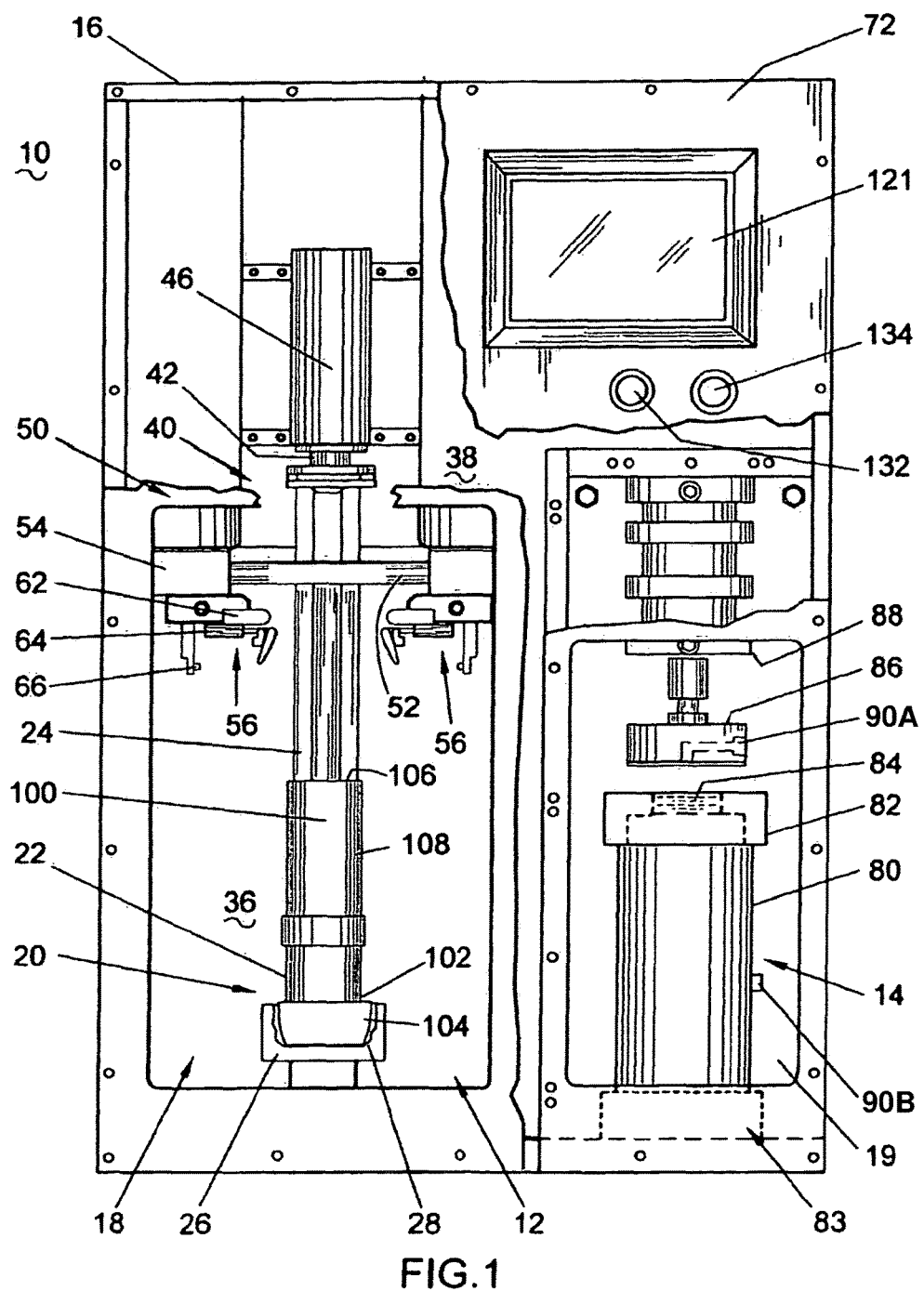
FIG. 1 illustrates a front elevation view with the front panel cut away showing the major electro-mechanical elements of a plastic tube sealing and test system according to an embodiment of the invention.
Figure 2:
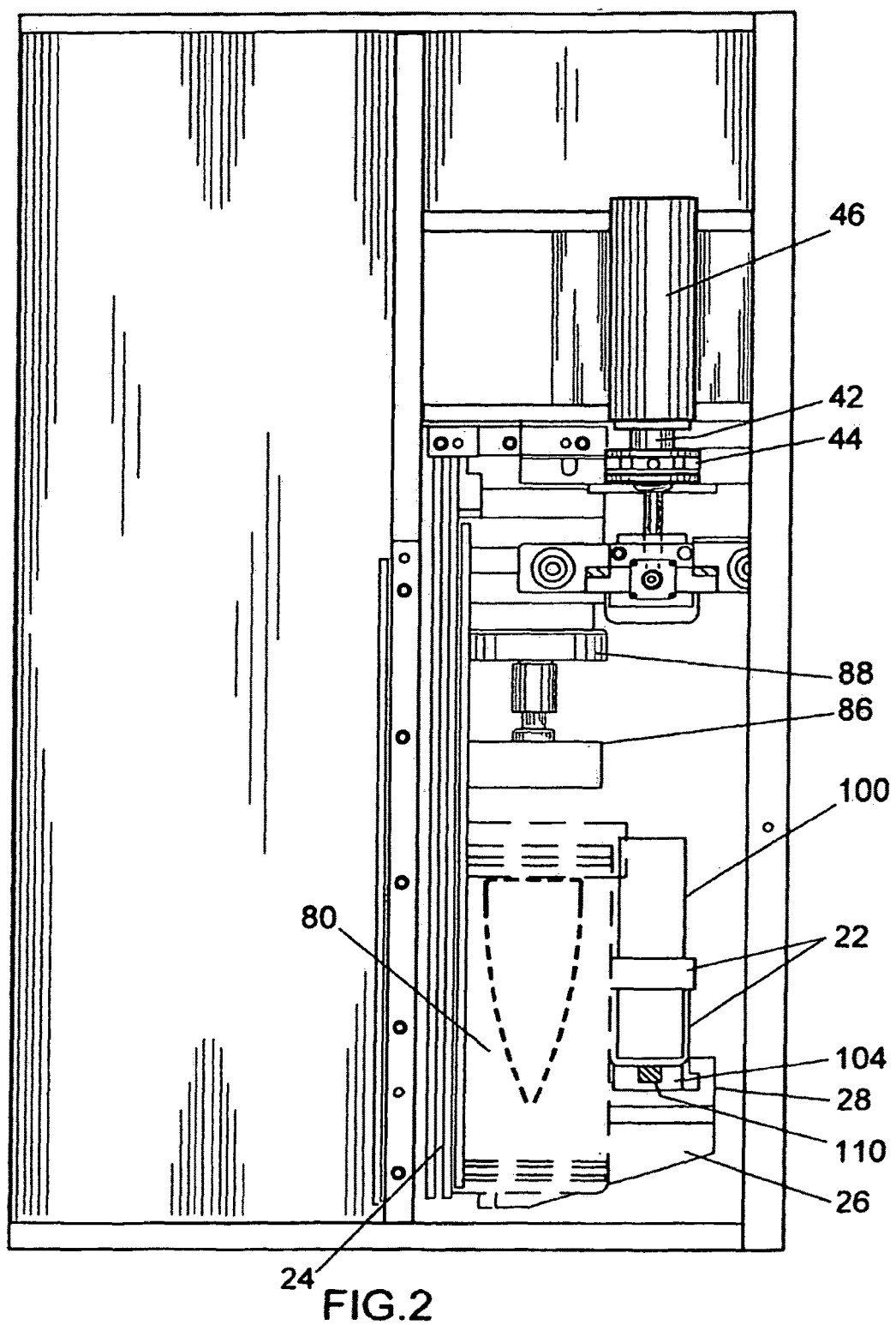
FIG. 2 illustrates a side elevation view with side panel removed of the system according to an embodiment of the invention.
Figure 3:
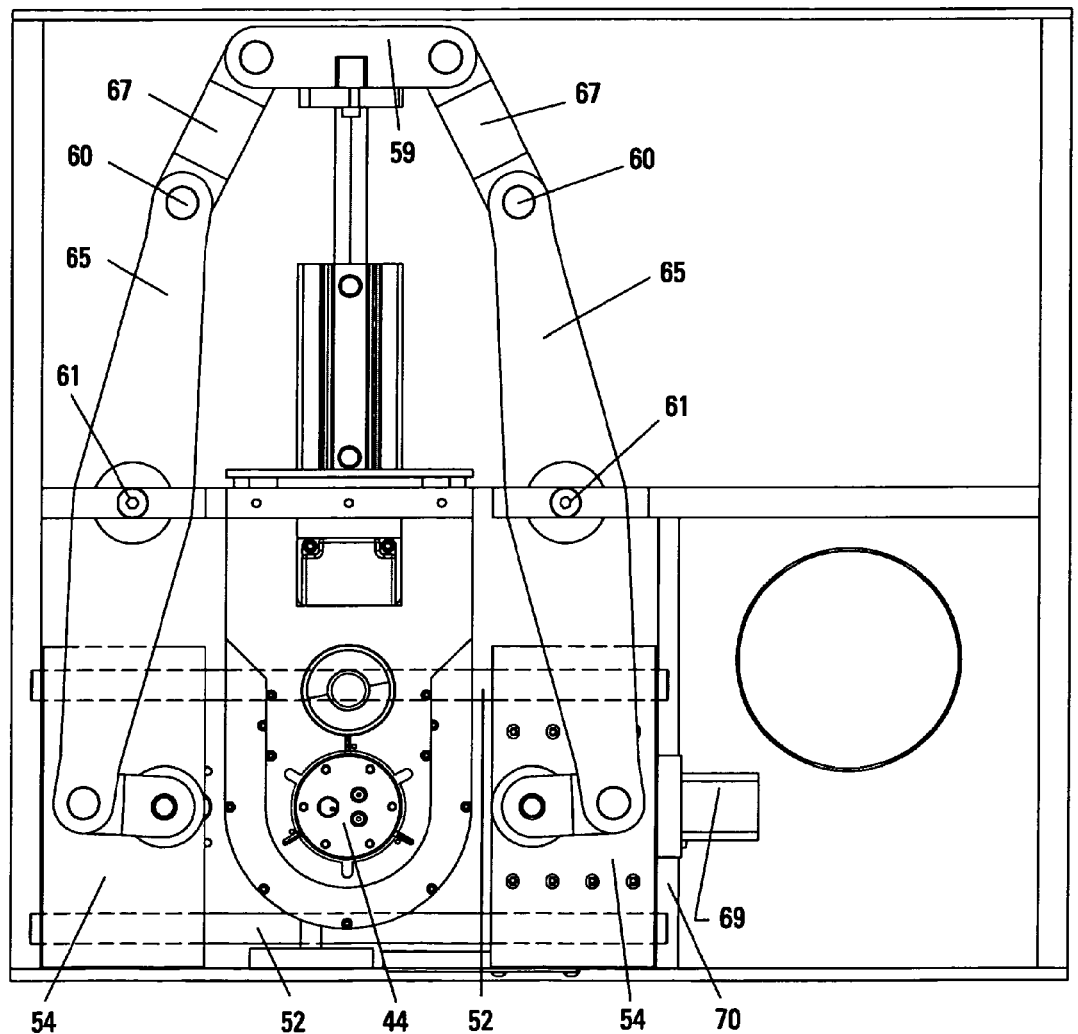
FIG. 3 illustrates a top view with the top panel removed of a portion of the electro-mechanical elements of the system according to an embodiment of the invention.
Figure 4:
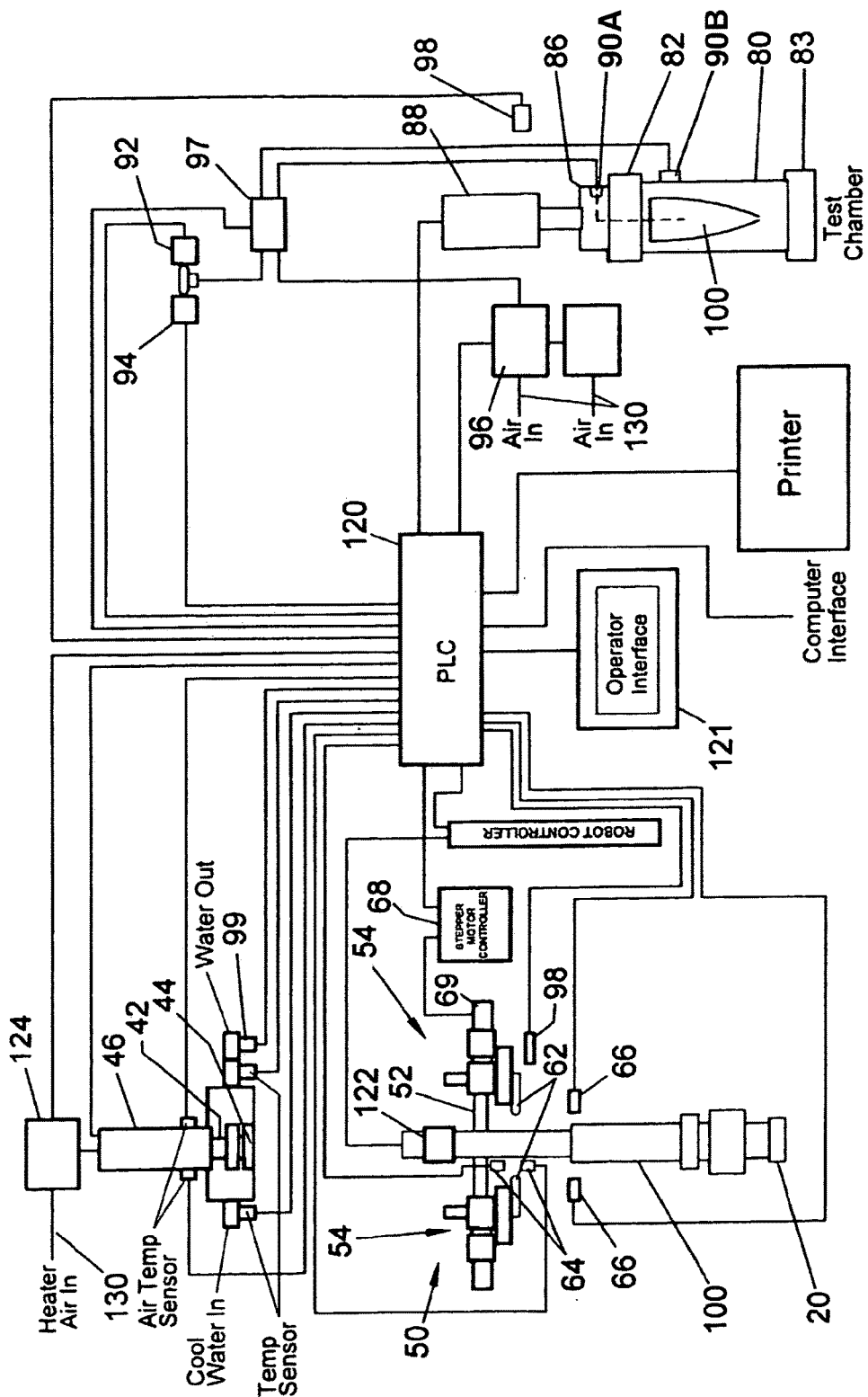
FIG. 4 illustrates a schematic of the electrical and fluid elements of the system according to an embodiment of the invention.
Figure 5:
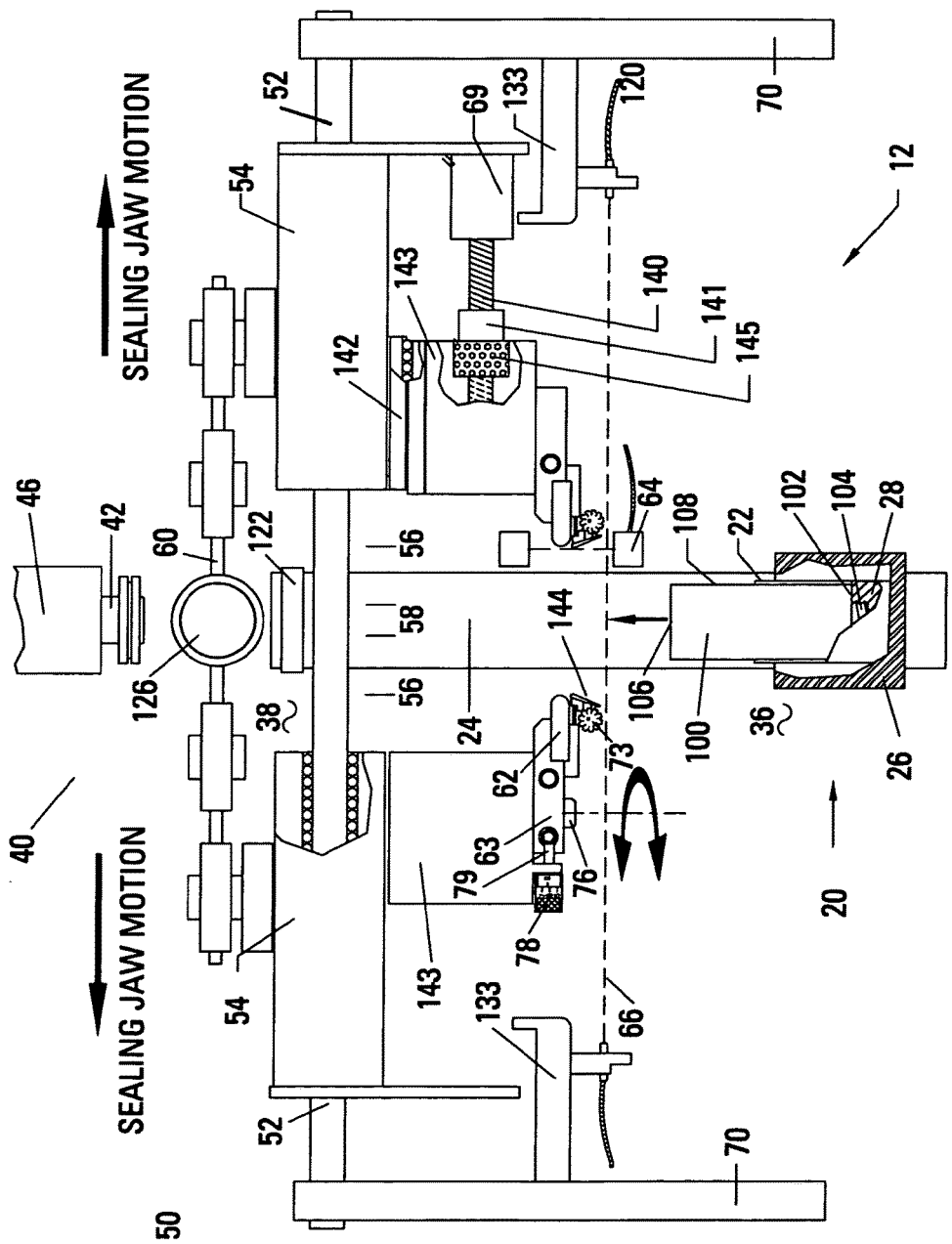
FIG. 5 illustrates a schematic of the tube sealing apparatus according to an embodiment of the invention.
Figure 6:
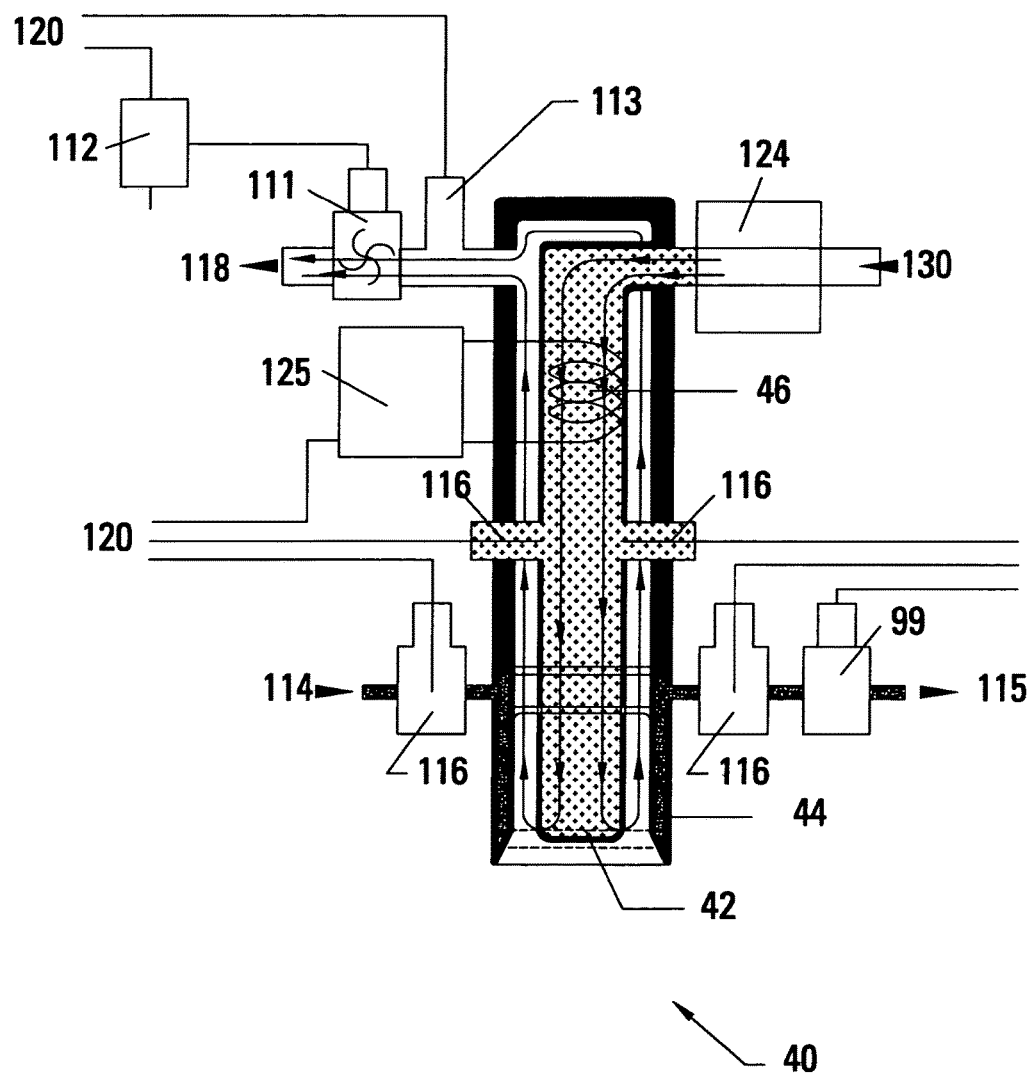
FIG. 6 illustrates a schematic of a tube heating apparatus according to an embodiment of the invention.
Figure 7:
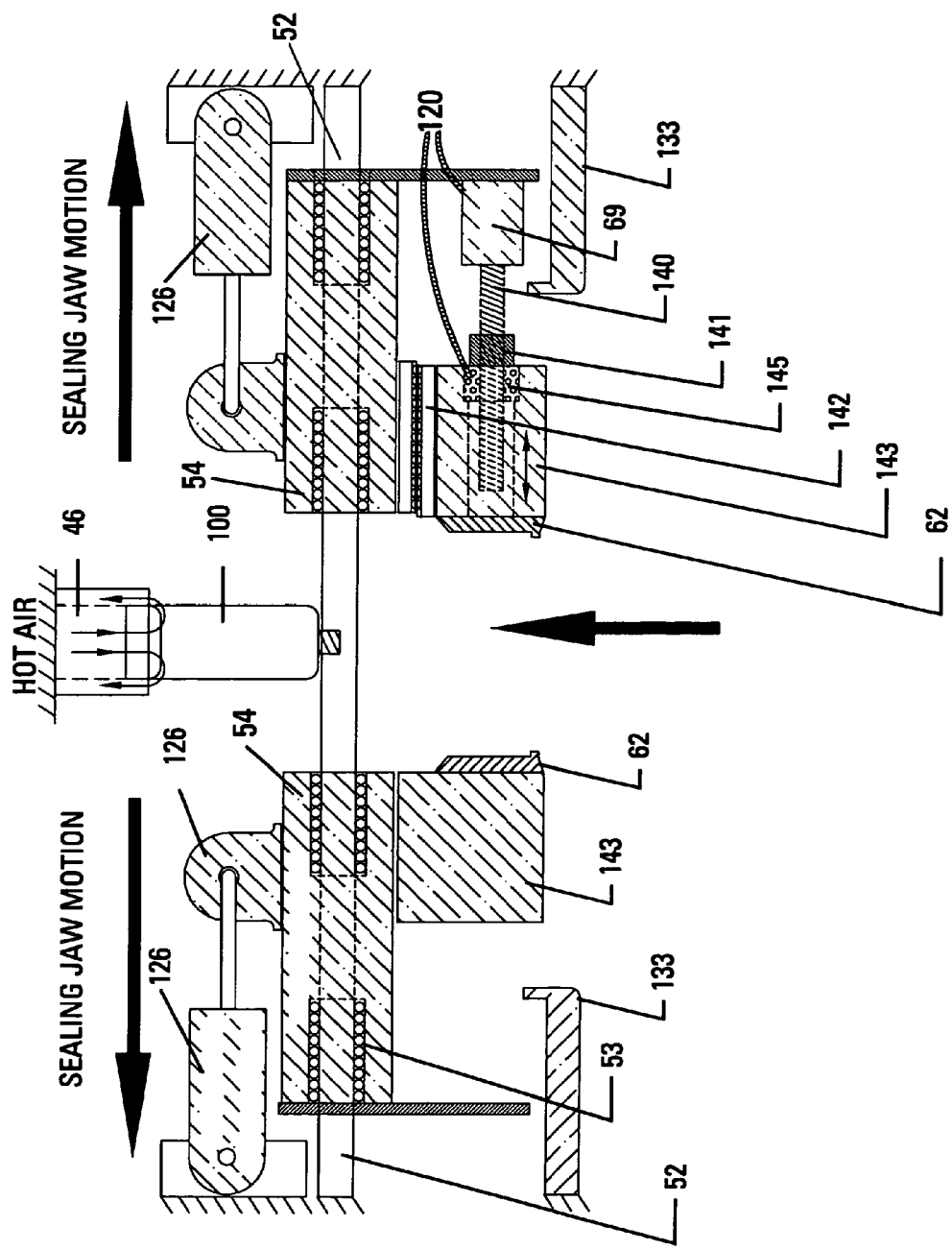
FIG. 7 illustrates a schematic of a clamping apparatus with a tube positioned in a heater nozzle according to an embodiment of the invention.
Figure 8:
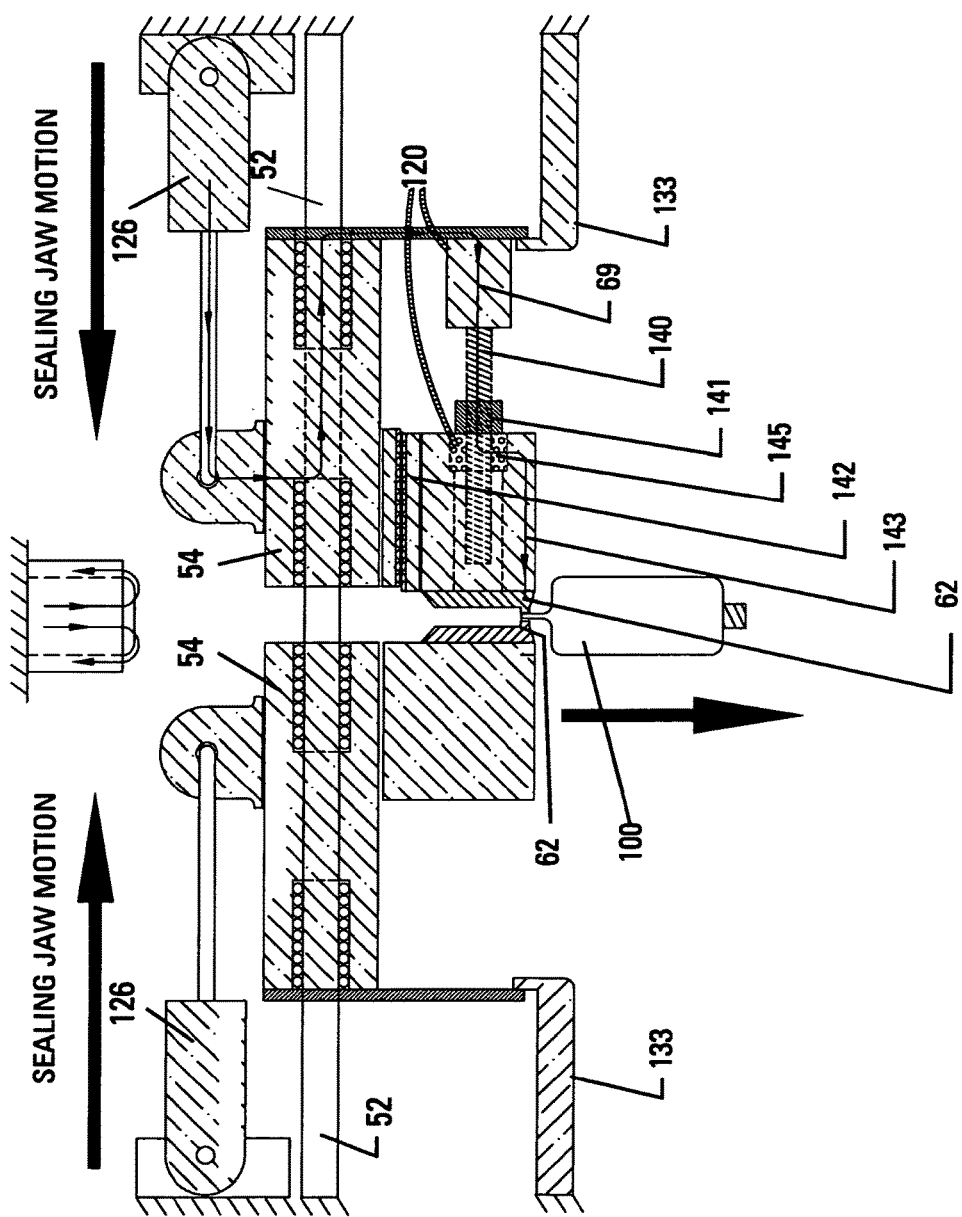
FIG. 8 illustrates a schematic of a clamping apparatus with a tube positioned in opposed clamp jaws according to an embodiment of the invention.

The following detailed description represents the best currently contemplated modes for carrying out the invention. The description is not to be taken in a limiting sense, but is made merely for the purpose of illustrating the general principles of the invention.

Referring to FIGS. 1 through 9, a tube sealing apparatus 12 is illustrated as positioned in the left portion of a combined tube sealing and test system 10 enclosure or housing and a tube seal and wall strength test apparatus 14 is illustrated as positioned in the right portion. While for purposes of this description the two apparatus 12, 14 are illustrated in a combined housing 16, it may be understood that each may also be used separately for purposes such as sealing tubes in an assembly operation if modified or testing tubes sealed for example on an assembly line.

The tube sealing apparatus 12 may have a tube sealing positioning apparatus 20 with a tube holder 22 slideably attached to a vertical guide 24 that extends from a generally lower portion 36 of the sealing chamber 18 to an upper portion 38 adjacent a tube heating apparatus 40. The tube holder 22 may be raised and lowered in the sealing chamber 18 using a hydraulic or pneumatic device, an electric motor device or other suitable linear positioning device 122. The tube holder 22 may have a generally horizontal holder 26 for receipt of a tube mouth end fixture 28 into which the mouth end 102 of a plastic tube 100 may be inserted. Multiple fixtures 28 may be used that may be sized to receive various shapes and sizes of tube mouth ends 102 including the cap 104 of a tube 100 if attached to the mouth end 102.

The tube heating apparatus 40 may be positioned in the upper portion 38 of the sealing chamber 18 positioned for a plastic tube 100 raised by the tube holder 22 to have the open end 106 positioned adjacent a heater nozzle 42 of an air heater element 46. The heater nozzle 42 may be a replaceable or interchangeable attached nozzle to allow attachment of nozzle sizes and shapes to mate with different configuration plastic tubes 100. The heating device 46 may be an electric heating element that is controlled by heater control module 125. The heating device 46 receives air from an air blower or compressed air 130 from an air flow control device 124 as may be understood in the art that may be controlled by a processor 120 that may be a digital processor, microprocessor, computer or the like that may be connected to a display device 121. A cooling ring 44 may be positioned around the heating nozzle 42 as an element to cool the outside wall 108 of the plastic tube 100. Cooling water is input at inlet port 114 and is circulated around cooling ring 44. The water temperature is monitored by temperature sensors 116. The flow rate of water is monitored by water pressure sensor 99 and the water exits the tube heating apparatus through outlet port 115. The hot air is removed from the area around the cooling ring 44 with the aid of a negative air pressure device 111 such as a fan or air venture mounted on top of the heating device 46. The air flow is controlled by air flow controller 112 and the amount of air is measured by air flow sensor 113. The heated air exits the heating device 46 through the negative pressure device 111 and exit port 118.

Intermediate the tube positioning apparatus 20 and the heating apparatus 40, a clamping apparatus 50 or crimping apparatus may be positioned to press or crimp the open end 106 plastic wall 108 to fuse the open end in a heat seal manner. The clamping apparatus 50 may have one or more generally horizontal bars 52 attached to opposed frames 70 of the housing 16. Two opposed clamping devices 54 may be slidably mounted on the bars 52 and may be moved from an open position 56 to an approximately closed position 58 by a lever arm device 60 that rotates on fixed pins 61. The lever arm device 60 has the structure of a toggle clamp action wherein the members 65, 67 are attached to cross member 59 to be toggle clamp powered by a clamp positioning device 126, for example, a hydraulic or pneumatic actuator. The clamping apparatus 50 moves the clamping devices 54 to a position 58 as controlled by fixed stops 133.

The opposed clamping devices 54 may each have a clamping or sealing jaw 62 located to be positioned adjacent to each other at a distance commanded by the processor 120. The spacing distance of the two jaws 62 when moved to a position adjacent may be calculated based on the parameters of each type of plastic tube 100. For purposes of positioning and control the clamping devices 54 may have a spacing distance sensor 64 such as a laser gap sensor and may have a tube position sensor 66 such as an optical sensor to detect the top of the open end 106 of a tube 100.

The tube sealing apparatus 12 may have a plastic tube 100 positioned on the tube holder 22; the tube holder 22 may be raised until the open end 106 of the tube 100 is sensed by the tube position sensor 66 that is connected to the processor 120. The sensor 66 is used to determine the distance to the heater nozzle 42 or the distance from the tube holder 22 to the open end 106; the tube holder 22 may then be moved to place the open end 106 adjacent the heater nozzle 42 to heat the tube 100 for a defined time; when the defined time has elapsed, the tube 100 may be lowered to position the tube wall 108 area adjacent the open end 106 between the jaws 62; and the jaws 62 may be closed to a predetermined distance and maintained in a clamped position for a predetermined time to seal the tube 100. As clamp jaws 62 close on the tube 100, pre-fold jaws 144 shape the tube 100 from a round to an oval form insuring both an aesthetic and uniform seal. The pre-fold jaws 144 are adjustable and calibrated to provide validation for future sealing process setup. There is a selector wheel 73 to adjust the angle of the pre-fold jaws 144 relative to vertical. The sealing jaws 62 are attached to sealing jaw holder 63. The sealing jaws 62 and sealing jaw holder 63 may have one or both holders 63 attached to the jaw support blocks 143 by a pivot pin 76 to allow the sealing jaws 62 to be non-parallel when a tube 100 is therebetween to allow for tube wall 108 thickness variations. A vernier dial with post 78 and a tab stop 79 allows small and repeatable adjustments of the relative angle of a sealing jaw 62. A tube 100 sealed in this process may then be tested in a vacuum or pressure chamber apparatus to determine the strength of the sealed tube 100.

The processor 120 may have software or firmware modules for controlling the tube holder 22 movement and positioning, for example, a loop crimping gap setting module, that receives signals from the spacing distance sensor 64 and a stepper motor control device 68 that may control an electric motor 69 to move the clamping apparatus 50. An operator may enter the desired gap, or distance between clamp jaws 62, at the operator interface 121. The opposing clamp device 54 close to a position 58 resting on hard stops 133. The motor 69 turns a threaded shaft 140 in a threaded nut 141 to push jaw support block 143 to the desired gap setting position. The jaw support block 143 slides on the slide bearing assembly 142. There may also be parts per minute based timing for sealing process module 74 to control the time for tube 100 heating and for jaw 62 clamp time to simulate production cycling for tube sealing as well as to vary timing to test improved sealing parameters or marginal production process times. There may be temperature control program modules to sense and allow control of hot air temperature 125 or fluid control for heating the tube 100. A data processing software module may control and collect data, such as crimp gap during crimping, temperature during tube heating and heating change during crimping time.

Figure 9:
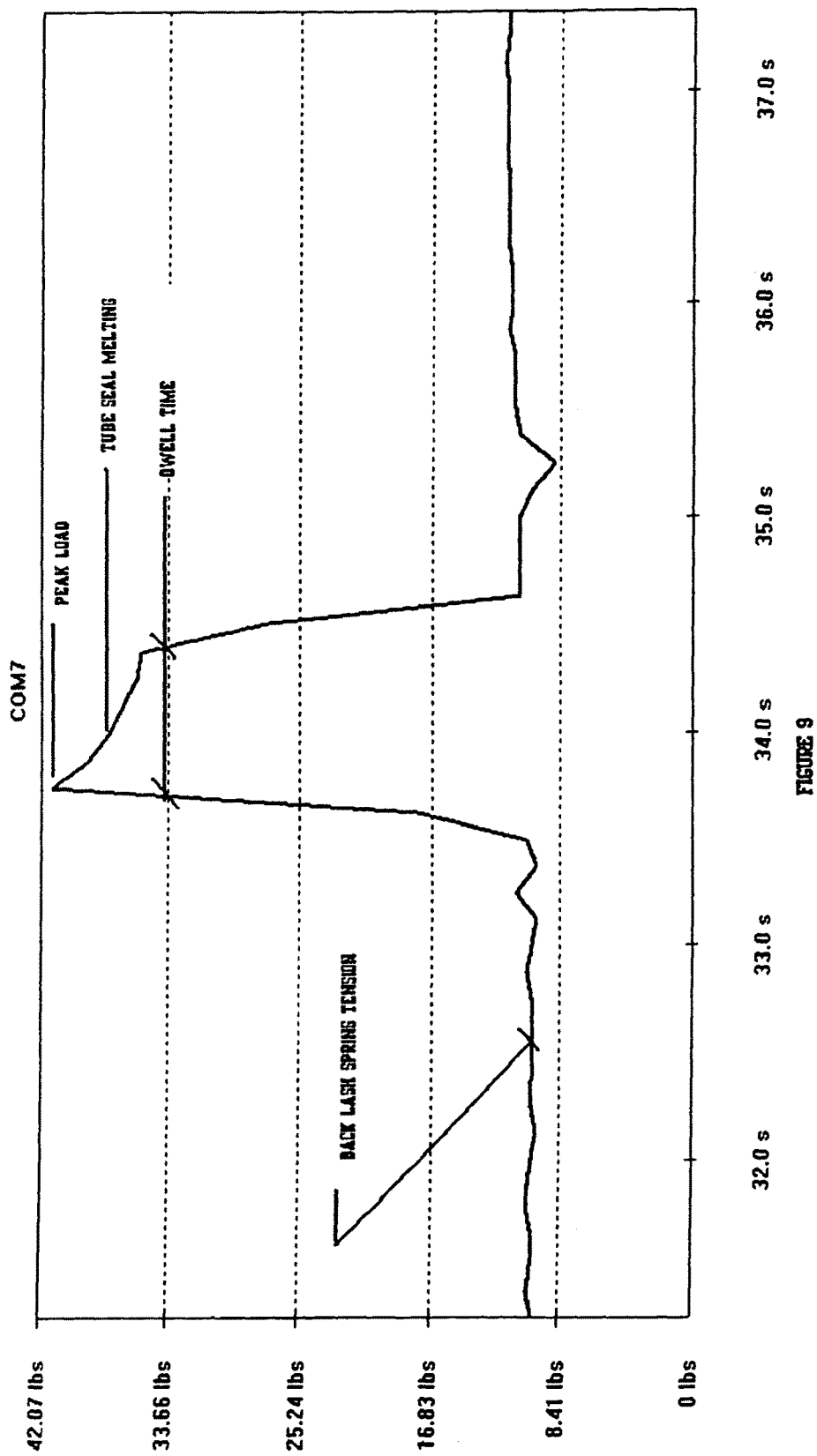
FIG. 9 illustrates a graph of the sealing pressure versus time for sealing a tube according to an embodiment of the invention.

A sensor that may be a load force sensing device 145 may be attached to the threaded nut 141 and may be connected to the control processor 120. When the clamping devices 54 are positioned against the hard stops 133 the force of the clamp jaws 62 against a tube 100 while in the second adjacent closed position 58 is transferred to the jaw support block 143 and thereby to the load force sensing device 145 that converts the load force to a signal that is transmitted to the control processor 120. The parameters of time for clamp jaws 62 in the first spaced apart position 56 and the second adjacent closed position 58 and the load force when in the second adjacent closed position as recorded by the control processor may be displayed in a graphical form of the load force, Y-axis, versus the tube processing time, X-axis. This graphical representation may display the dwell time during tube sealing during which time the interior wall of a tube 100 melts and welds together and the combined wall thickness of the sealed end reduces with a resultant measured pressure decrease of the clamp jaws 62. This is illustrated as a decreasing slope during dwell time on FIG. 9. These parameter characteristics are caused by factors of temperature, tube materials and structure, jaw gap and the like. The parameters as may be displayed graphically as illustrated in FIG. 9 may be used as a template, when proper sealing parameters for desired sealing results for a type of tube have been determined, to compare to measured parameters for subsequent tube sealing operation of an apparatus to monitor proper operation.

A tube seal and wall strength test apparatus 14 may be used in a stand alone test station to test tubes 100 or may be integrated with a tube sealing apparatus 14 as illustrated in the Drawings. The tube test apparatus 14 may have a test container 80 that may be generally cylindrical in shape with a top cover 82 removable and having an attachment aperture 84 therein for threadable attachment of a threaded mouth 110 of a plastic tube 100.

The top cover 82 and attachment aperture 84 may have other attachment mechanisms for attachment of non-threaded tubes 100. A tube 100 may be attached at a mouth end 102 in the attachment aperture 84 and the top cover 82 may be placed on the test container 80 with the tube 100 in the test container 80. The test container 80 may then be positioned in the tube test apparatus 14. A sealing disk 86 controlled by a position activator 88, such as a hydraulic or pneumatic piston, may be positioned on the top cover 82 to close the aperture 84. The sealing disk 86 may have one or more ports 90a in communication with the tube mouth 100 to allow fluid pressure to be applied to the interior of the tube 100, and one or more ports 90b can be in communication with the interior of the test container 80 to allow a vacuum to be applied in the test container 80. The ports 90a and 90b may be connected to a vacuum pump or venturi 128 and a fluid, for example, compressed air, source 130.

The processor 120 may have software or firmware modules for controlling the test apparatus 14 pressure and vacuum testing, for example, a module to allow entering; pressure and vacuum set points, speed of ramp up to pressure or vacuum, and dwell time at set points. There may be a data output of the vacuum transmitter 92 and pressure transmitter 94 to the processor 120 for use in control of vacuum and pressure and to detect a sudden change when a tube 100 fails or there may be a leak of pressure or vacuum. A data processing software module may control and collect data, such as failure pressure or vacuum, test time and time of failure, and failure type that may be entered by a user to indicate tube wall or tube seal failure.

The tube test system 10 may have a display 121 on the front panel 72 for use in display of apparatus settings, test results, switch images for touch panel control, as well as display of other elements, for example, an internal processor 120 program functions and status. An emergency stop switch 132 and an on/off switch 134 may also be located on the front panel. The sealing chamber 18 and test chamber 19 may have movable doors for closing to protect a user from any unexpected circumstances. The doors may have sensors 98 that signal the processor 120 to inhibit operation of the tube sealing apparatus 12 and test apparatus 14 if the door is not closed. Also, a water pressure sensor 99 may signal the processor 120 to turn off the heating apparatus 40. The processor 120 may be programmed to return the horizontal holder 26 to the lower portion 36 of the sealing chamber 18 at the end of the sealing process or if the sealing process is interrupted. These processes may be considered to be safety features.

The positioning of the tube sealing apparatus 12 elements may be useful for production of sealed product tubes 100. Current practice appears to move tubes from a heating station to a sealing station. This two step process may not be as repetitively reliable as the combination heating and sealing in one apparatus as described.

While the invention has been particularly shown and described with respect to the illustrated embodiments thereof, it will be understood by those skilled in the art that the foregoing and other changes in form and details may be made therein without departing from the spirit and scope of the invention.

We claim:

1. A system for testing a strength of a sealed tube, comprising:
    a test container having an open interior space and an aperture to receive a mouth of the sealed tube;
    a sealing disk having a first fluid port, the sealing disk configured to be engaged with the test container to fluidically couple the first fluid port to the aperture and to seal the open interior space;
    a source of a pressurized fluid, the source fluidically coupled to the first fluid port; and
    a control processor to control a speed of a ramp up of a pressure of the pressurized fluid in the sealed tube until a failure of the sealed tube occurs, wherein the control processor is configured to receive a data output representing a pressure in the test container outside the sealed tube, and wherein the control processor is configured to receive a data output representing the pressure of the pressurized fluid in the sealed tube.

2. The system of claim 1 wherein the control processor is configured to receive input indicating a set point for the pressure of the pressurized fluid in the sealed tube.

3. The system of claim 2 wherein the control processor is configured to receive input indicating a dwell time for the set point.

4. The system of claim 1 wherein the control processor is configured to receive input indicating the speed of the ramp up.

5. The system of claim 1 wherein the mouth of the sealed tube is positioned within the aperture and the sealed tube is positioned within the open interior space.

6. The system of claim 5 wherein the mouth of the sealed tube is threadedly engaged with the aperture.

7. The system of claim 1 wherein the source of the pressurized fluid is a source of pressurized air.

8. The system of claim 1 wherein the sealing disk is controlled by a position actuator.

9. The system of claim 1 wherein the failure of the sealed tube is a failure of a wall of the sealed tube.

10. The system of claim 1 wherein the failure of the sealed tube is a failure of a seal of the sealed tube.

11. The system of claim 1 wherein the control processor is configured to detect a sudden change in the pressure of the pressurized fluid in the sealed tube and the control processor is configured to output a failure pressure of the pressurized fluid in the sealed tube.

12. The system of claim 1 wherein the control processor is configured to receive input indicating a failure type.

13. The system of claim 1 wherein the test container includes a removable cover and the removable cover includes the aperture.

14. A method of testing a strength of a sealed tube, comprising:
    positioning a mouth of the tube within an aperture in a test container;
    positioning the tube within an open interior space of the test container;
    engaging a sealing disk with the test container to fluidically couple a first fluid port of the sealing disk with the aperture in the test container;
    fluidically coupling a source of compressed air to the first fluid port;

controlling a speed of a ramp up of a pressure of the compressed air in the sealed tube until a failure of the sealed tube occurs;

communicating a data output representing the pressure of the compressed air in the sealed tube to a control processor; and communicating a data output representing a pressure in the test container outside the sealed tube to the control processor.

15. The method of claim 14 wherein controlling the speed includes using the control processor to control the speed.

16. The method of claim 14, further comprising receiving input indicating a set point for the pressure of the compressed air in the sealed tube.

17. The method of claim 16, further comprising receiving input indicating a dwell time for the set point.

18. The method of claim 14, further comprising receiving input indicating the speed of the ramp up.

19. The method of claim 14, further comprising controlling the sealing disk by a position actuator.

20. The method of claim 14 wherein the failure of the sealed tube is a failure of a wall of the sealed tube.

21. The method of claim 14 wherein the failure of the sealed tube is a failure of a seal of the sealed tube.

22. The method of claim 14, further comprising detecting a sudden change in the pressure of the compressed air in the sealed tube and outputting a failure pressure of the compressed air in the sealed tube.

23. The method of claim 14, further comprising receiving input indicating a failure type.

24. The method of claim 14 wherein the test container includes a removable cover and the removable cover includes the aperture.

* * * * *